United States Patent
Cortés Provencio

(10) Patent No.: US 8,711,178 B2
(45) Date of Patent: Apr. 29, 2014

(54) SYSTEM AND METHOD FOR GENERATING PROFILE MORPHING USING CEPHALOMETRIC TRACING DATA

(75) Inventor: Emilio David Cortés Provencio, Albacete (ES)

(73) Assignee: Dolphin Imaging Systems, LLC, Chatsworth, CA (US)

( * ) Notice: Subject to any disclaimer, the term of this patent is extended or adjusted under 35 U.S.C. 154(b) by 0 days.

(21) Appl. No.: 13/111,751

(22) Filed: May 19, 2011

(65) Prior Publication Data

US 2012/0223970 A1 Sep. 6, 2012

Related U.S. Application Data

(63) Continuation of application No. PCT/ES2011/070133, filed on Mar. 1, 2011.

(30) Foreign Application Priority Data

Mar. 1, 2011 (ES) .................................. 201130273

(51) Int. Cl.
*G09G 5/00* (2006.01)

(52) U.S. Cl.
USPC ........... 345/646; 345/647; 345/473; 345/474; 345/475

(58) Field of Classification Search
USPC .................................. 345/646, 647, 473–475
See application file for complete search history.

(56) References Cited

U.S. PATENT DOCUMENTS

| | | | |
|---|---|---|---|
| 5,278,756 A | 1/1994 | Lemchen et al. | 364/413.28 |
| 5,342,202 A | 8/1994 | Deshayes | 434/270 |
| 5,825,941 A | 10/1998 | Linford et al. | 382/294 |
| 7,134,874 B2 * | 11/2006 | Chishti et al. | 433/24 |
| 7,234,937 B2 | 6/2007 | Sachdeva et al. | 433/24 |

(Continued)

FOREIGN PATENT DOCUMENTS

| | | | |
|---|---|---|---|
| JP | 2001283191 | 10/2001 | |
| JP | 2009165558 | 7/2009 | |
| WO | WO 99/59106 | 11/1999 | G06T 15/00 |
| WO | WO 01/80765 | 11/2001 | |
| WO | WO 02/03304 | 1/2002 | G06F 19/00 |
| WO | WO 2005/025404 | 3/2005 | |

OTHER PUBLICATIONS

James L. Ackerman, William R. Proffit, "Soft tissue limitations in orthodontics: Treatment planning guidelines", vol. 67 No. 5 1997, p. 327-336.*

International Search Report and Written Opinion; Application No. PCT/ES2011/070133; pp. 10, Nov. 24, 2011.

Xia et al.; "Three-dimensional Virtual Reality Surgical Planning and Simulation Workbench for Orthognathic Surgery"; Int J Adult Orthod Orthognath Surg, vol. 15, No. 4; pp. 265-282, 2000.

(Continued)

*Primary Examiner* — Antonio A. Caschera
*Assistant Examiner* — Weiming He
(74) *Attorney, Agent, or Firm* — Baker Botts L.L.P.

(57) ABSTRACT

A method for generating an animated morph between a first image and a second image is provided. The method may include: (i) reading a first set of cephalometric landmark points associated with the first image; (ii) reading a second set of cephalometric landmark points associated with the second image; (iii) defining a first set of line segments by defining a line segment between each of the first set of cephalometric landmarks; (iv) defining a second set of line segments by defining a line segment between each of the second set of cephalometric landmarks such that each line segment of the second set of line segments corresponds to a corresponding line segment of the first set of line segments; and (v) generating an animation progressively warping the first image to the second image based at least on the first set of line segments and the second set of line segments.

17 Claims, 4 Drawing Sheets

(56) References Cited

U.S. PATENT DOCUMENTS

| | | |
|---|---|---|
| 7,953,260 B2 | 5/2011 | Weinzweig et al. ............ 382/128 |
| 2001/0007451 A1 | 7/2001 | Aono .............................. 345/442 |
| 2002/0090123 A1 | 7/2002 | Bazin .............................. 382/128 |
| 2005/0018902 A1 | 1/2005 | Liang .............................. 382/154 |
| 2005/0244794 A1 | 11/2005 | Kemp et al. ................... 433/217.1 |
| 2006/0215014 A1* | 9/2006 | Cohen et al. ................... 348/14.08 |
| 2006/0280351 A1 | 12/2006 | Luping et al. .................. 382/128 |
| 2007/0299551 A1 | 12/2007 | Weinzweig et al. ............ 700/90 |
| 2008/0025592 A1 | 1/2008 | Jerebko et al. ................. 382/132 |
| 2008/0118143 A1 | 5/2008 | Gordon et al. ................. 382/154 |
| 2008/0285829 A1 | 11/2008 | Wang et al. .................... 382/131 |
| 2009/0136108 A1 | 5/2009 | Badiei et al. ................... 382/131 |
| 2010/0145898 A1 | 6/2010 | Malfliet et al. ................. 706/47 |
| 2011/0045428 A1 | 2/2011 | Boltunov et al. ............... 433/24 |
| 2011/0194787 A1 | 8/2011 | Chun et al. ..................... 382/284 |
| 2011/0285711 A1 | 11/2011 | Kilgard .......................... 345/426 |
| 2012/0257841 A1 | 10/2012 | Liao ............................... 382/293 |
| 2012/0259592 A1 | 10/2012 | Liao ............................... 703/1 |

OTHER PUBLICATIONS

United States Office Action; U.S. Appl. No. 13/081,895; pp. 12, Sep. 4, 2012.

International Search Report and Written Opinion; PCT/US2012/031942; pp. 11, Oct. 4, 2012.

International Search Report and Written Opinion; PCT/US2012/031945; pp. 8, Oct. 4, 2012.

Hwang et al.; "Maxillocfacial 3-dimensional image analysis for the diagnosis of facial asymmetry"; American Journal of Orthodontics and Dentofacial Orthopedics; 130 (6); 779-785, Jun. 28, 1905, Dec. 2006.

Xia et al.; "Computer-assisted three-dimensional surgical planning and simulation"; Int. J. Oral Maxillofac. Surg.; vol. 29; pp. 250-258, Jun. 22, 1905, Aug. 2000.

International Preliminary Report on Patentability; PCT/ES2011/070133; pp. 5, Sep. 12, 2013.

\* cited by examiner

SYSTEM AND METHOD FOR GENERATING PROFILE MORPHING USING CEPHALOMETRIC TRACING DATA

CROSS REFERENCE TO RELATED APPLICATION

This application is a continuation of copending International Application No. PCT/ES2011/070133 filed Mar. 1, 2011 which designates the United States. This application is also copending with Spanish application number 201130273 filed Mar. 1, 2011. The contents of these applications are hereby incorporated by reference in its entirety.

TECHNICAL FIELD

The present disclosure relates in general to dentofacial imaging, and more particularly to systems and methods for surgical planning using dentofacial imaging.

BACKGROUND

Dentofacial surgery, also referred to as oral and maxillofacial surgery, is often employed to correct a wide spectrum of diseases, injuries and defects in the head, neck, face, jaws and the hard and soft tissues of the oral and maxillofacial region of humans or other non-human patients. As capabilities of computers and software improve, practitioners of dentofacial surgery increasingly use computer-aided dentofacial imaging tools in order to model dentofacial features of patients, diagnose diseases, injuries, and defects, plan dentofacial surgical procedures and other treatments, and educate patients regarding diagnoses and treatments.

For example, to educate a patient regarding a potential change in physical appearance resulting from dentofacial treatment, a practitioner may desire to present the patient with a "before" image of the patient prior to treatment, an "after" image depicting the patient following treatment, and an animation or "morph" between the before and after images. Traditionally, morphing is accomplished by manually marking key features on a first image, such as the contour of the nose or location of an eye, and manually mark where these same points existed on the second image, creating multiple pairs of line segments. Software would then create an animation whereby the first image would slowly distort to have the features of the second image at the same time that it cross-faded between the two images. However, such manual marking of features may be time-consuming and thus, undesirable.

As another example, to plan and simulate a dentofacial surgery, a practitioner may, with the aid of a computer-aided tool, virtually modify various bones or bone segments of the patient via a user interface of a computer. Such computer-aided planning and simulation may allow a practitioner to simulate effect of various surgical adjustments on a patient, including effects on a patient's aesthetic appearance.

SUMMARY

In accordance with the teachings of the present disclosure, disadvantages and problems associated with traditional approaches to surgical planning using dentofacial imaging may be substantially reduced or eliminated.

In accordance with embodiments of the present disclosure, a method for generating an animated morph between a first image and a second image is provided. The method may include: (i) reading a first set of cephalometric landmark points associated with the first image; (ii) reading a second set of cephalometric landmark points associated with the second image; (iii) defining a first set of line segments by defining a line segment between each of the first set of cephalometric landmarks; (iv) defining a second set of line segments by defining a line segment between each of the second set of cephalometric landmarks such that each line segment of the second set of line segments corresponds to a corresponding line segment of the first set of line segments; and (v) generating an animation progressively warping the first image to the second image based at least on the first set of line segments and the second set of line segments.

In accordance with additional embodiments of the present disclosure, an article of manufacture may include a non-transitory computer-readable medium; and computer-executable instructions carried on the computer-readable medium. The instructions may be executable by one or more processors and may be configured to cause the one or more processors to: (i) read a first set of cephalometric landmark points associated with the first image; (ii) read a second set of cephalometric landmark points associated with the second image; (iii) define a first set of line segments by defining a line segment between each of the first set of cephalometric landmarks; (iv) define a second set of line segments by defining a line segment between each of the second set of cephalometric landmarks such that each line segment of the second set of line segments corresponds to a corresponding line segment of the first set of line segments; and (v) generate an animation progressively warping the first image to the second image based at least on the first set of line segments and the second set of line segments.

In accordance with further embodiments of the present disclosure, a computing system may comprise a processor and a memory communicatively coupled to the processor. The memory may have stored thereon a program of instructions configured to, when executed by the processor: (i) read a first set of cephalometric landmark points associated with the first image; (ii) read a second set of cephalometric landmark points associated with the second image; (iii) define a first set of line segments by defining a line segment between each of the first set of cephalometric landmarks; (iv) define a second set of line segments by defining a line segment between each of the second set of cephalometric landmarks such that each line segment of the second set of line segments corresponds to a corresponding line segment of the first set of line segments; and (v) generate an animation progressively warping the first image to the second image based at least on the first set of line segments and the second set of line segments.

Other technical advantages will be apparent to those of ordinary skill in the art in view of the following specification, claims, and drawings.

BRIEF DESCRIPTION OF THE DRAWINGS

A more complete understanding of the present embodiments and advantages thereof may be acquired by referring to the following description taken in conjunction with the accompanying drawings, in which like reference numbers indicate like features, and wherein.

DETAILED DESCRIPTION

Figure 1:
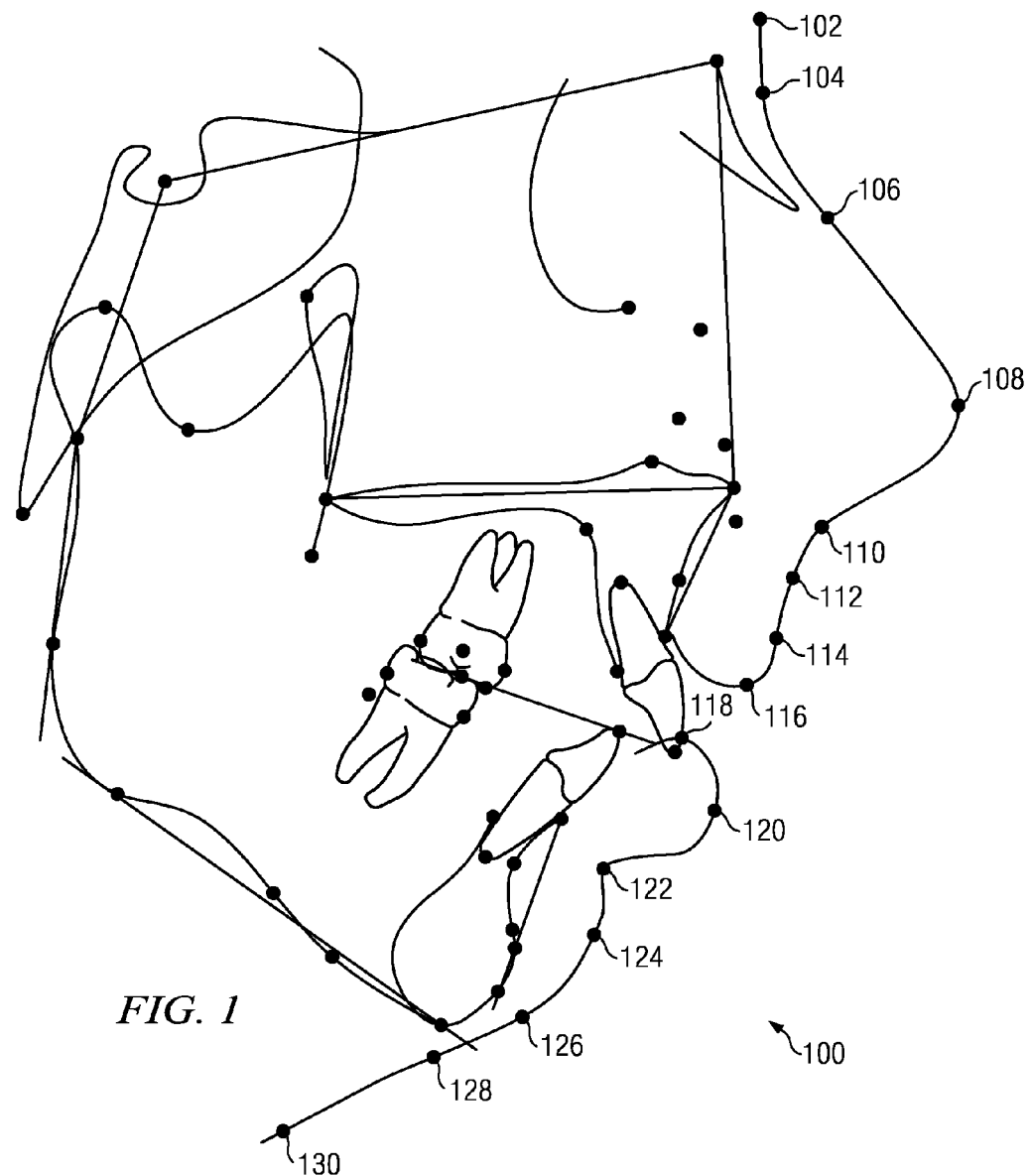
FIG. 1 illustrates an example cephalometric tracing of soft tissue and bone features of a profile view of an individual, in accordance with embodiments of the present disclosure.

FIG. 1 illustrates an example cephalometric tracing 100 of soft tissue and bone features of a profile view of an individual, in accordance with embodiments of the present disclosure. A cephalometric tracing may be drawn based on a radiograph or other image of the tissues of an individual's head or otherwise extracted from such radiograph or other image, and may be used to study relationships between bony and soft tissue landmarks to diagnose facial growth abnormalities prior to treatment, in the middle of treatment to evaluate progress, or at the conclusion of treatment to ascertain that the goals of treatment have been met. As shown in FIG. 1, such landmarks may include, without limitation:

soft tissue glabella 102—surface of the soft tissue covering the most anterior point of the frontal bone (e.g., between an individual's eyebrows);

soft tissue nasion 104—the soft tissue profile's most concave point at the bridge of the nose;

bridge of nose 106—mid-point of soft tissue nasion 104 to pronasale 108 (e.g., the first contour encountered along the length of the profile of the nose);

pronasale 108—most anterior point of curve of nose (e.g., tip of nose);

subnasale 110—point at which the nose connects to the center of upper lip;

soft tissue A-point 112—most concave point between subnasale 110 and upper lip 114;

upper lip 114—most anterior point on the curve of the upper lip;

stomion superius 116—most inferior point on the curve of the upper lip;

stomion inferius 118—most superior point on the curve of the lower lip;

lower lip 120—most anterior point on the curve of the lower lip;

soft tissue B-point 122—most concave point between lower lip 120 and soft tissue pogonion 124;

soft tissue pogonion 124—most anterior point on the anterior curve of the soft tissue chin;

soft tissue gnathion 126—midpoint between the soft tissue pogonion 124 and the soft tissue mention 128;

soft tissue menton 128—the most inferior point of the soft tissue chin; and throat point 130—intersection of lines tangent to the neck and the throat.

In some embodiments, cephalometric tracing 100 may be created by or with the assistance of a computer-aided surgical planning tool executing on a computer. For example, the computer-aided surgical planning tool may read a radiograph or other image and based on the content of such image, generate one or more portions of a cephalometric tracing and/or identify one or more cephalometric landmarks. Alternatively or in addition, the computer-aided surgical planning tool may display a radiograph or other image and a practitioner may, via a user interface of the surgical planning tool, use the image as a guide to construct the cephalometric tracing of the bony and soft tissue features and/or identify one or more cephalometric landmarks. The computer-aided surgical planning tool may store (e.g., to a computer-readable medium) the cephalometric tracing, the cephalometric landmarks, and/or their associated coordinates.

Figure 2:
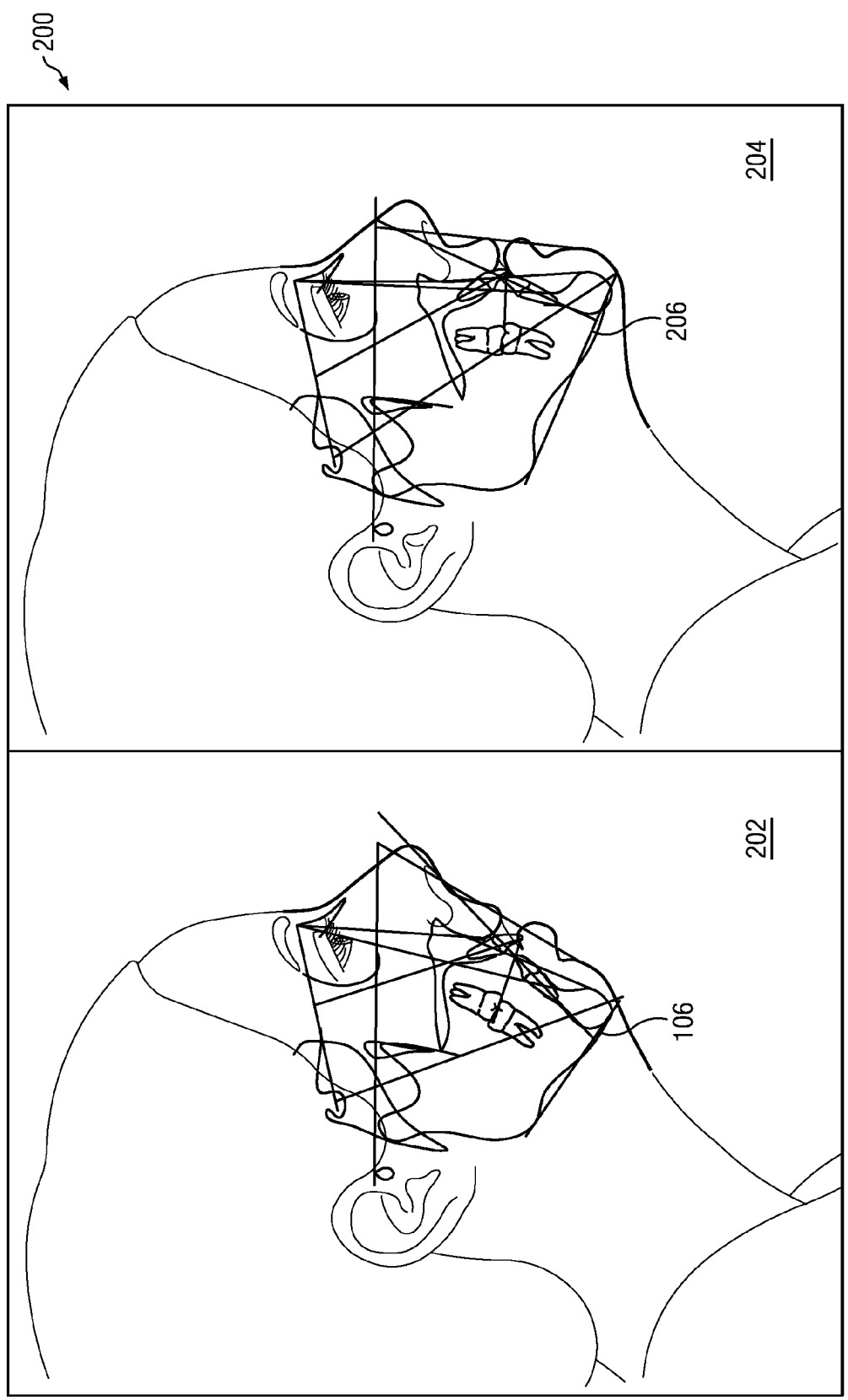
FIG. 2 illustrates an example user interface screen 200 of a computer-aided surgical planning tool, in accordance with embodiments of the present disclosure.

FIG. 2 illustrates an example user interface screen 200 of a computer-aided surgical planning tool, in accordance with embodiments of the present disclosure. As shown in FIG. 2, user interface screen 200 may include a pre-surgical profile image 202 of an individual with the pre-surgical cephalometric tracing 100 of FIG. 1 overlaid upon image 202, and a planned post-surgical image 204 of the same individual with a planned post-surgical cephalometric tracing 206 overlaid upon image 204.

Pre-surgical profile image 202 may be generated by taking a profile photograph of the subject individual. The computer-aided surgical planning tool may be configured to read the image (e.g., from a computer-readable medium) and, in response to user input, overlay cephalometric tracing 100 upon image 202. In some embodiments, the surgical planning tool may be configured to detect and align corresponding features of image 202 and cephalometric tracing 100 and align image 202. In other embodiments, the surgical planning tool may be configured to permit a user via a user interface to adjust image 202 and/or cephalometric tracing 100 in order to align features. Once image 202 and cephalometric tracing 100 are aligned as desired, various cephalometric landmarks (e.g., landmarks 102-130) may be stored as part of profile image 202 (e.g., as metadata in a digital file of profile image 202).

Planned post-surgical cephalometric tracing 206 may be created from pre-surgical cephalometric tracing 100 by a practitioner interacting with the computer-aided surgical planning tool to modify (e.g., with a mouse or other similar user input device) cephalometric tracing 100 and/or locations of cephalometric landmarks to obtain desired post-surgical characteristics. For example, computer-aided surgical planning tool may warp cephalometric tracing 100 in response to user input, according to well-known methods. The computer-aided surgical planning tool may store (e.g., to a computer-readable medium) planned post-surgical cephalometric tracing 206 and its associated cephalometric landmarks (as modified).

Planned post-surgical image 204 may be created from pre-surgical image 202 based on differences between planned post-surgical cephalometric tracing 206 and pre-surgical cephalometric tracing 100. For example, based on differences of locations of elements of cephalometric tracings 100 and 206 and/or differences in locations of cephalometric landmarks, computer-aided surgical planning tool may warp image 202 according to well-known methods to align corresponding features of planned post-surgical image 204 and planned post-surgical cephalometric tracing 206. After creation of planned post-surgical image, the computer-aided surgical planning tool may store (e.g., to a computer-readable medium) modified cephalometric landmarks as part of planned post-surgical image 204 (e.g., as metadata in a digital file of planned post-surgical image 204).

Figure 3A:
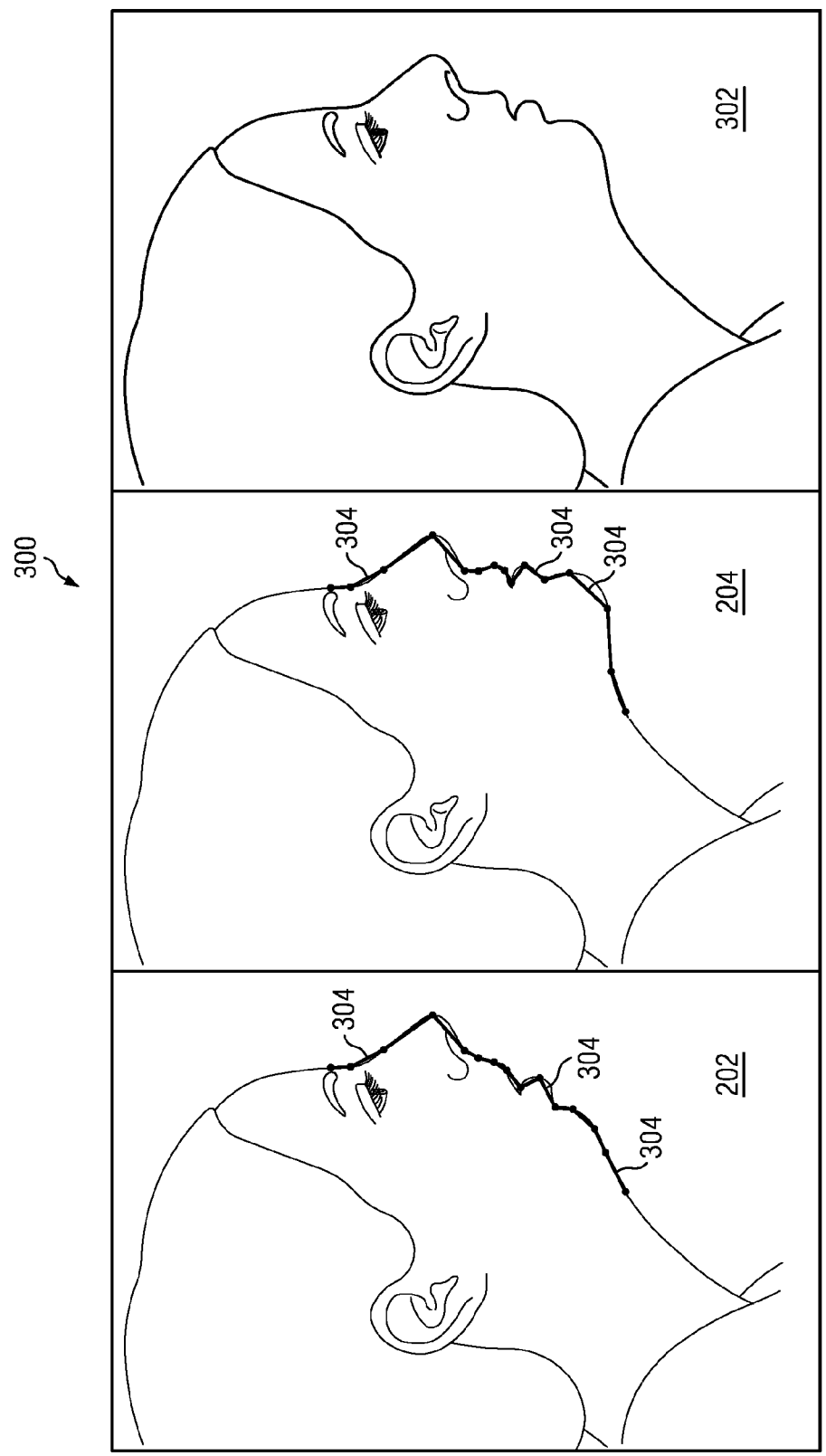
FIGS. 3A and 3B illustrate another example user interface screen of a computer-aided surgical planning tool, in accordance with embodiments of the present disclosure.
Figure 3B:
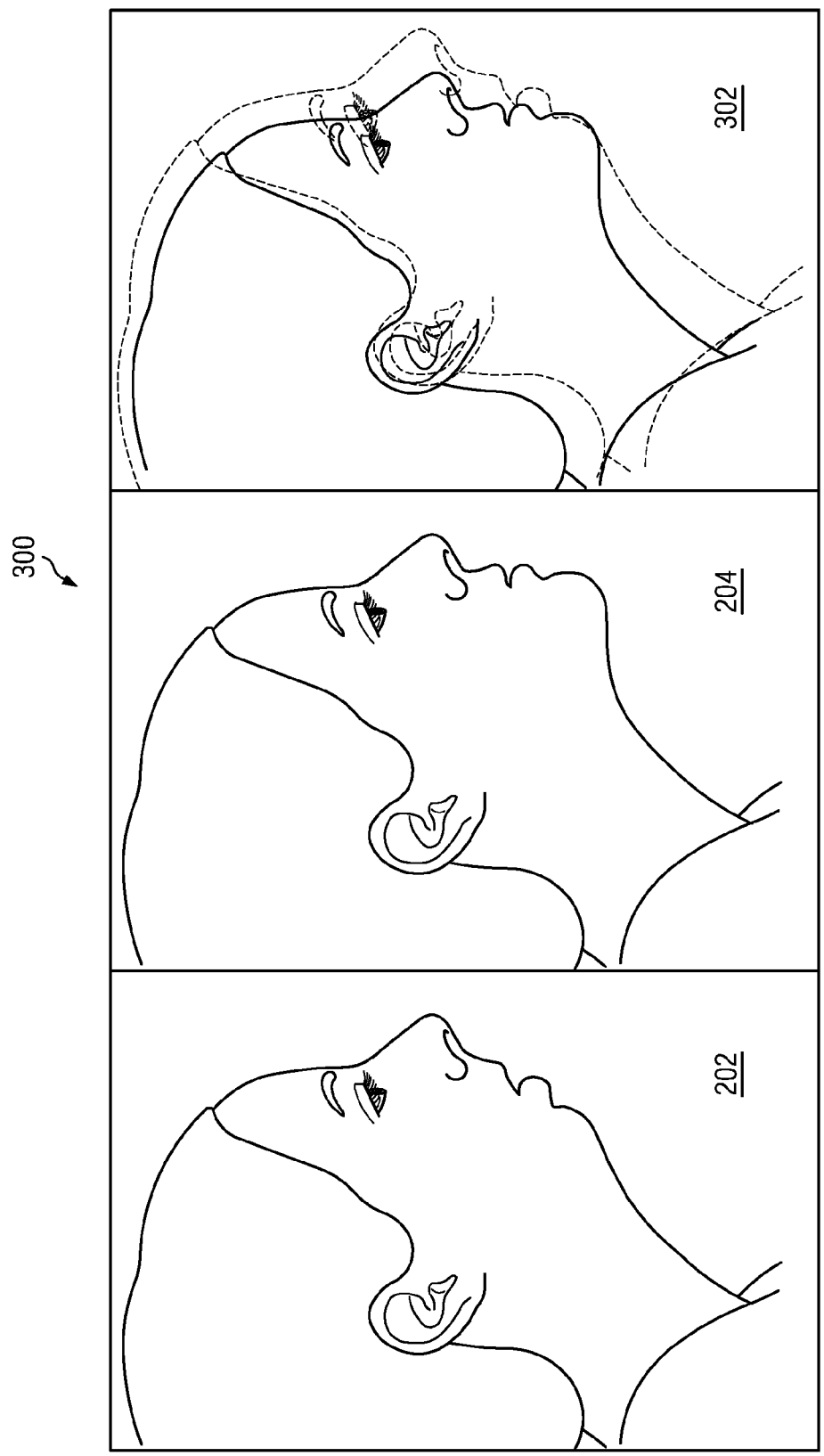

FIGS. 3A and 3B illustrate another example user interface screen 300 of a computer-aided surgical planning tool, in accordance with embodiments of the present disclosure. As shown in FIG. 3A, user interface screen 300 may include three panes displaying pre-surgical image 202, planned post-surgical image 204, and animation mid-point frame image 302. Also as shown in FIG. 3A, the computer-aided surgical planning tool may also load and display on each of pre-surgical image 202 and planned post-surgical image 204 various cephalometric landmarks 102-130 and line segments 304 between adjacent cephalometric landmarks. Accordingly, each line segment 304 of image 202 has a corresponding line segment 304 in image 204 (e.g., line segment 304 between soft tissue glabella 102 and soft tissue nasion 104 of image 202 corresponds to line segment 304 between soft tissue glabella 102 and soft tissue nasion 104 of image 204, and so on).

As is known in the art, metamorphosis from one image to another (e.g., creating a "morph") typically includes creation of an animation that gradually cross-dissolves between the first image and the second image, while at the same time warping the first image into the second image. Thus, often the middle frame of the animation is an average of the first image distorted and cross-faded halfway towards the second image and the second image distorted and cross-faded halfway towards the first image.

As is known in the art, warping from one image to another may include establishing one or more line segments on the first image each associated with a particular feature, and a corresponding line segment in the second image for each line segment of the first image. Each intermediate frame of the animation may defined by creating a new set of line segments by interpolating the line segments from their positions in the first image to their positions in the second image. Both images are distorted toward the position of the line segments in each intermediate frame, and the two resulting images are cross-dissolved throughout the animation. Each pixel of the images may be distorted by a rotation, translation, and/or a scale based on its distance and relationship to each of the line segments.

To facilitate creation of an animation between pre-surgical image 202 and planned post-surgical image 204, the computer-aided surgical planning tool may, as described above, generate a plurality of line segments 304 for pre-surgical image 202 and a plurality of corresponding line segments 304 for post-surgical image 204 based on cephalometric landmarks and display such line segments 304. In addition, the computer-aided surgical planning tool may allow a user to define and display additional pairs of line segments for other features (e.g., an ear, hairline, clothing neckline, etc.) to further enhance the quality of the animation.

In addition, as described above, the computer-aided surgical planning tool may display animation mid-point frame image 302. Mid-point frame image 302 may represent the middle frame of the animation between image 202 and image 204 using the corresponding pairs of line segments 304 generated by the computer-aided surgical planning tool and any corresponding pairs of line segments defined by a user. Such mid-point frame image 302 may provide a visual guide to the user, potentially identifying features for which a user may desire to define associated line segments in order to create a higher-quality animation. For example, mid-point frame image 302 may indicate areas of non-overlap or ghosting of the halfway-distorted pre-surgical image 202 and halfway-distorted planned post-surgical image 204 for which a user may define additional pairs of line segments.

Generation of line segments 304 by the computer-aided surgical planning tool may reduce the effort required by a user to generate an animation, as it may reduce or eliminate the need for a user to define numerous line segments required for a quality metamorphosis between images. This advantage may be seen by reference to FIG. 3B, which depicts mid-point frame image 302 in the absence of line segment 304 pairs in images 202 and 204. As evident from FIG. 3B, the absence of line segment 304 pairs in images 202 and 204 may lead to significant areas of non-overlap or ghosting of the halfway-distorted pre-surgical image 202 and halfway-distorted planned post-surgical image 204, requiring a user to manually define many line segment pairs in order to create a quality animation.

Figure 4:
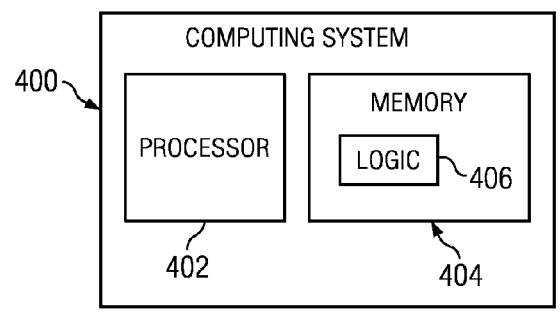
FIG. 4 depicts a block diagram of an example computing system, in accordance with embodiments of the present disclosure.

FIG. 4 depicts a block diagram of an example computing system 1200, in accordance with embodiments of the present disclosure. Computing system 1200 may be used in whole or part to provide or perform various functions and operations described above with respect to FIGS. 1-3B. As shown in FIG. 12, computing system 1200 may include processor 1202, memory 1204, and logic 1206.

Computing system 1200 may comprise any suitable combination of hardware and/or software implemented in one or more modules to provide or perform the functions and operations described above with respect to FIGS. 1-3B. In some embodiments, computing system 1200 may comprise a mainframe computer, general-purpose personal computer (PC), a Macintosh, a workstation, a Unix-based computer, a server computer, or any suitable processing device. In some embodiments, the functions and operations described above may be performed by a pool of multiple computing systems 1200.

Memory 1200 may comprise any suitable arrangement of random access memory (RAM), read only memory (ROM), magnetic computer disk, CD-ROM, or other magnetic, optical or solid state storage media, or any other volatile or non-volatile memory devices that store one or more files, lists, tables, or other arrangements of information. Although FIG. 4 illustrates memory 1204 as internal to computing system, it should be understood that memory 1204 may be internal or external to computing system 1200, depending on particular implementations. Memory 1204 may be separate from or integral to other memory devices to achieve any suitable arrangement of memory devices for use in providing or performing desired operations or functionality.

Memory 1204 may be further operable to store logic 1206. Logic 1206 generally comprises rules, algorithms, code, tables, and/or other suitable instructions executable by processor 1202 to provide or perform the functions and operations described above with respect to FIGS. 1-3B.

Memory 1204 may be communicatively coupled to processor 1202. Processor 1202 may be generally operable to execute logic to perform operations described herein. Processor 1202 may comprise any suitable combination of hardware and software implemented in one or more modules to provide the described function or operation.

Although the present disclosure has been described in detail, it should be understood that various changes, substitutions, and alterations can be made hereto without departing from the spirit and the scope of the invention as defined by the appended claims.

What is claimed is:

1. A method for generating an animated morph between a first image and a second image, comprising:
   displaying in a first pane the first image while simultaneously displaying the second image in a second pane on a computer display screen;
   reading a first set of cephalometric landmark points associated with the first image;
   reading a second set of cephalometric landmark points associated with the second image;
   defining a first set of line segments by defining a line segment between each of the first set of cephalometric landmarks;
   aligning the first set of line segments with the first image and displaying the aligned first set of line segments with the first image in the first pane;
   defining a second set of line segments by defining a line segment between each of the second set of cephalometric landmarks such that each line segment of the second set of line segments corresponds to a corresponding line segment of the first set of line segments, and a length of at least one line segment of the second set of line segments is different from a length of the corresponding line segment of the first set of line segments, the second set of line segments generated before a surgery and associated with post-surgery placement of cephalometric landmarks;

aligning the second set of line segments with the second image and displaying the aligned second set of line segments with the second image in the second pane while simultaneously displaying the first image and the aligned first set of line segments in the first pane; and generating an animation, by a processor, progressively warping the first image to the second image based at least on the first set of line segments and the second set of line segments, comprising:

displaying an intermediate frame image in a third pane while simultaneously displaying the aligned first set of line segments and the first image in the first pane and the second image and the aligned second set of line segments in the second pane;

detecting one of ghosting or non-overlap in the intermediate frame image;

in response to one of ghosting or non-overlap in the intermediate frame image, generating a set of line segments particular to the intermediate frame, the set of line segments defined by interpolating the first set of line segments and the second set of line segments;

distorting each pixel of the first image based at least on the position of the pixel relative to first set of line segments and the set of line segments particular to the intermediate frame;

distorting each pixel of the second image based at least on the position of the pixel relative to second set of line segments and the set of line segments particular to the intermediate frame; and cross-dissolving the pixel-distorted first Image and pixel-distorted second Image.

2. A method according to claim 1, wherein:
the first set of cephalometric landmark points are stored as metadata of the first image; and
the second set of cephalometric landmark points are stored as metadata of the second image.

3. A method according to claim 1, wherein location of the first set of cephalometric landmark points and second set of cephalometric landmark points are based at least on a cephalometric tracing of a patient's cranio-facial features.

4. A method according to claim 1, wherein location of the first set of cephalometric landmark points and second set of cephalometric landmark points are based at least on a radiograph of a patient's cranio-facial features.

5. A method according to claim 1, further comprising receiving input from a user, the input defining additional line segments of the first set of line segments and corresponding additional line segments of the second set of line segments.

6. A method according to claim 1, wherein distorting a pixel comprises at least one of rotating, translating, and scaling the pixel.

7. An article of manufacture comprising:
a non-transitory computer-readable medium; and
computer-executable instructions carried on the computer-readable medium, the instructions executable by one or more processors and configured to cause the one or more processors to:

display in a first pane the first image while simultaneously displaying the second image in a second pane;

read a first set of cephalometric landmark points associated with the first image;

read a second set of cephalometric landmark points associated with the second image;

define a first set of line segments by defining a line segment between each of the first set of cephalometric landmarks;

align the first set of line segments with the first image and display the aligned first set of line segments with the first image in the first pane;

define a second set of line segments by defining a line segment between each of the second set of cephalometric landmarks such that each line segment of the second set of line segments corresponds to a corresponding line segment of the first set of line segments, and a length of at least one line segment of the second set of line segments is different from a length of the corresponding line segment of the first set of line segments, the second set of line segments generated before a surgery and associated with post-surgery placement of cephalometric landmarks;

aligning the second set of line segments with the second image and display the aligned second set of line segments with the second image in the second pane while simultaneously displaying the first image and the aligned first set of line segments in the first pane; and generate an animation progressively warping the first image to the second image based at least on the first set of line segments and the second set of line segments, comprising:

display an intermediate frame image in a third pane while simultaneously displaying the aligned first set of line segments and the first image in the first pane and the second image and the aligned second set of line segments in the second pane;

detect one of ghosting or non-overlap in the intermediate frame image;

in response to one of ghosting or non-overlap in the intermediate frame image, generate a set of line segments particular to the intermediate frame, the set of line segments defined by interpolating the first set of line segments and the second set of line segments;

distort each pixel of the first image based at least on the position of the pixel relative to first set of line segments and the set of line segments particular to the intermediate frame;

distort each pixel of the second image based at least on the position of the pixel relative to second set of line segments and the set of line segments particular to the intermediate frame; and cross-dissolve the pixel-distorted first image and pixel-distorted second image.

8. An article of manufacture according to claim 7, wherein:
the first set of cephalometric landmark points are stored as metadata of the first image; and
the second set of cephalometric landmark points are stored as metadata of the second image.

9. An article of manufacture according to claim 7, wherein location of the first set of cephalometric landmark points and second set of cephalometric landmark points are based at least on a cephalometric tracing of a patient's cranio-facial features.

10. An article of manufacture according to claim 7, wherein location of the first set of cephalometric landmark points and second set of cephalometric landmark points are based at least on a radiograph of a patient's cranio-facial features.

11. An article of manufacture according to claim 7, the instructions further configured to cause the one or more processors to receive input from a user, the input defining additional line segments of the first set of line segments and corresponding additional line segments of the second set of line segments.

12. An article of manufacture according to claim 7, wherein distorting a pixel comprises at least one of rotating, translating, and scaling the pixel.

13. A computing system, comprising:
   a processor; and
   a memory communicatively coupled to the processor and having stored thereon a program of instructions configured to, when executed by the processor:
      display in a first pane the first image while simultaneously displaying the second image in a second pane;
      read a first set of cephalometric landmark points associated with the first image;
      read a second set of cephalometric landmark points associated with the second image;
      define a first set of line segments by defining a line segment between each of the first set of cephalometric landmarks;
      align the first set of line segments with the first image and display the aligned first set of line segments with the first image in the first pane;
      define a second set of line segments by defining a line segment between each of the second set of cephalometric landmarks such that each line segment of the second set of line segments corresponds to a corresponding line segment of the first set of line segments, and a length of at least one line segment of the second set of line segments is different from a length of the corresponding line segment of the first set of line segments, the second set of line segments generated before a surgery and associated with post-surgery placement of cephalometric landmarks;
      align the second set of line segments with the second image and display the aligned second set of line segments with the second image in the second pane while simultaneously displaying the first image and the aligned first set of line segments in the first pane; and
      generate an animation progressively warping the first image to the second image based at least on the first set of line segments and the second set of line segments, comprising:
         display an intermediate frame image in a third pane while simultaneously displaying the aligned first set of line segments and the first image in the first pane and the second image and the aligned second set of line segments in the second pane;
         detect one of ghosting or non-overlap in the intermediate frame image;
         in response to one of ghosting or non-overlap in the intermediate frame image, generate a set of line segments particular to the intermediate frame, the set of line segments defined by interpolating the first set of line segments and the second set of line segments;
         distort each pixel of the first image based at least on the position of the pixel relative to first set of line segments and the set of line segments particular to the intermediate frame;
         distort each pixel of the second image based at least on the position of the pixel relative to second set of line segments and the set of line segments particular to the intermediate frame; and
         cross-dissolve the pixel-distorted first image and pixel-distorted second image.

14. A computing system according to claim 13, wherein:
   the first set of cephalometric landmark points are stored as metadata of the first image; and
   the second set of cephalometric landmark points are stored as metadata of the second image.

15. A computing system according to claim 13, wherein location of the first set of cephalometric landmark points and second set of cephalometric landmark points are based at least on a cephalometric tracing of a patient's cranio-facial features.

16. A computing system according to claim 13, wherein location of the first set of cephalometric landmark points and second set of cephalometric landmark points are based at least on a radiograph of a patient's cranio-facial features.

17. A computing system according to claim 13, the program further configured to, when executed by the processor, receive input from a user, the input defining additional line segments of the first set of line segments and corresponding additional line segments of the second set of line segments.

* * * * *